United States Patent
Shimada et al.

(10) Patent No.: US 10,342,710 B2
(45) Date of Patent: Jul. 9, 2019

(54) METHOD AND DEVICE FOR MANUFACTURING WORN ARTICLE

(71) Applicant: ZUIKO CORPORATION, Osaka (JP)

(72) Inventors: Takahiro Shimada, Osaka (JP); Susumu Honge, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 321 days.

(21) Appl. No.: 15/524,102

(22) PCT Filed: Nov. 6, 2015

(86) PCT No.: PCT/JP2015/081319
§ 371 (c)(1),
(2) Date: May 3, 2017

(87) PCT Pub. No.: WO2016/076224
PCT Pub. Date: May 19, 2016

(65) Prior Publication Data
US 2017/0348160 A1    Dec. 7, 2017

(30) Foreign Application Priority Data

Nov. 14, 2014 (JP) .................................. 2014-231570

(51) Int. Cl.
*A61F 13/15*    (2006.01)
*A61F 13/496*    (2006.01)

(52) U.S. Cl.
CPC .. *A61F 13/15764* (2013.01); *A61F 13/15601* (2013.01); *A61F 13/15699* (2013.01);
(Continued)

(58) Field of Classification Search
None
See application file for complete search history.

(56) References Cited

U.S. PATENT DOCUMENTS 5,046,272 A    9/1991    Vogt et al.
8,596,324 B2 *  12/2013   Yamamoto ........ A61F 13/15747
                                                156/199

(Continued)

FOREIGN PATENT DOCUMENTS

JP    2002-272781 A    9/2002
JP    2007-125407 A    5/2007

(Continued)

OTHER PUBLICATIONS

International Extended European Search Report for Application No. 15859274.1, dated Apr. 19, 2018.
(Continued)

*Primary Examiner* — Barbara J Musser
(74) *Attorney, Agent, or Firm* — Renner, Otto, Boisselle & Sklar, LLP

(57) ABSTRACT

A method including: a step of carrying first and second continuous webs in a carrying direction; a step of folding the continuous webs in two; a first attachment step, in which portions of first edges, which extend in the carrying direction of the continuous webs and which are to be leg holes of a worn article, are attached together intermittently in the carrying direction; a step of straightening, in a width direction, creases on one of the continuous web after the first attachment step; and a second attachment step, in which the continuous webs are attached together at least at portions along second edges opposite to the first edges, with the creases being straightened.

10 Claims, 11 Drawing Sheets

(52) U.S. Cl.
CPC .. *A61F 13/15723* (2013.01); *A61F 13/15739* (2013.01); *A61F 13/15747* (2013.01); *A61F 13/15804* (2013.01); *A61F 13/496* (2013.01); *A61F 2013/15715* (2013.01); *A61F 2013/15869* (2013.01); *A61F 2013/15878* (2013.01)

(56) References Cited

U.S. PATENT DOCUMENTS

| | | |
|---|---|---|
| 2002/0129888 A1 | 9/2002 | Otsubo et al. |
| 2002/0174930 A1 | 11/2002 | Umebayashi et al. |
| 2006/0254708 A1 | 11/2006 | Wada et al. |
| 2010/0038018 A1* | 2/2010 | Otsubo ............. A61F 13/15699 156/163 |
| 2010/0219224 A1 | 9/2010 | Yamamoto |
| 2012/0178609 A1 | 7/2012 | Yamamoto |

FOREIGN PATENT DOCUMENTS

| | | |
|---|---|---|
| JP | 2008-174328 A | 7/2008 |
| JP | 2011-030804 A | 2/2011 |
| WO | WO 2005-013871 A1 | 2/2005 |

OTHER PUBLICATIONS

International Search Report Issued in PCT/JP2015/081319 dated Jan. 26, 2016.

* cited by examiner

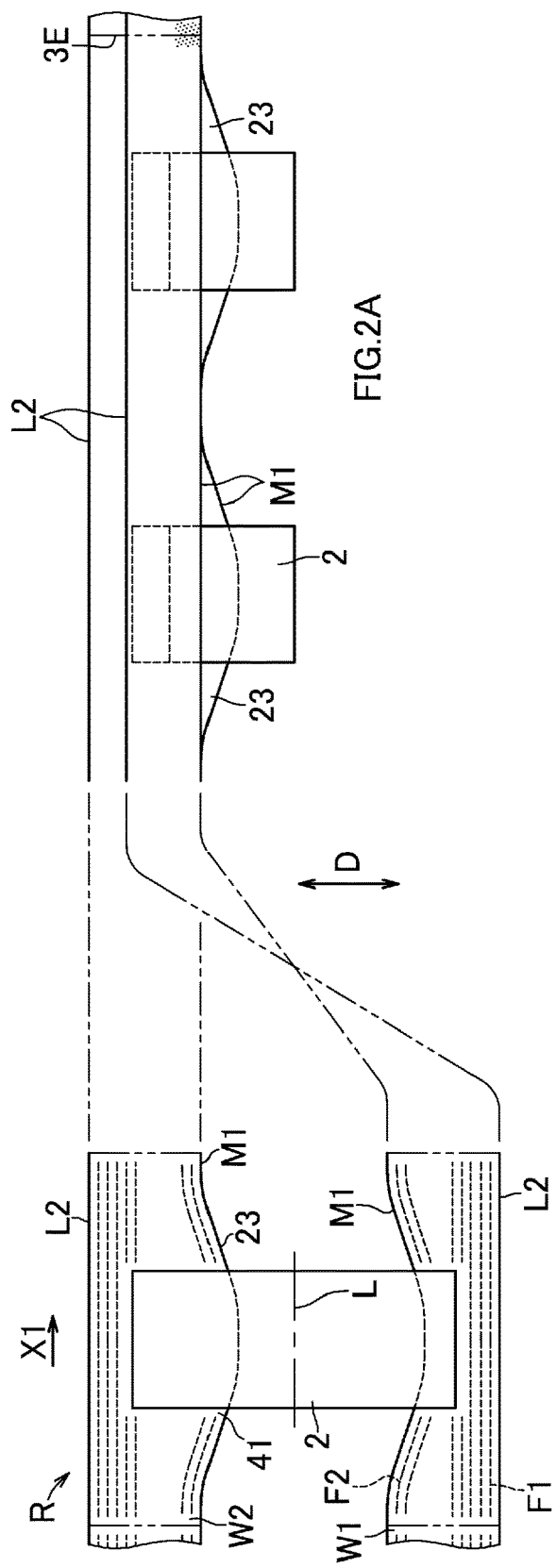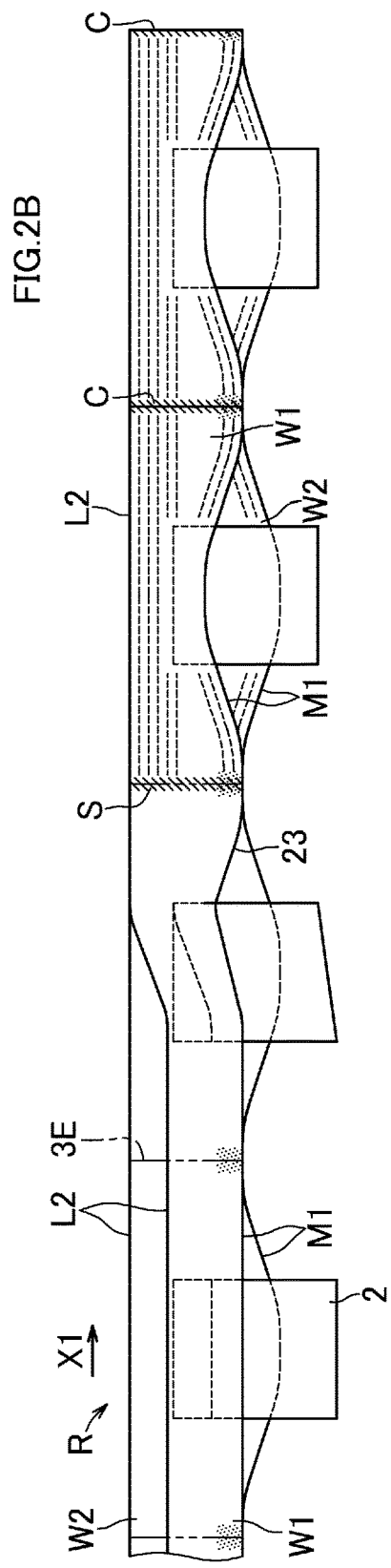

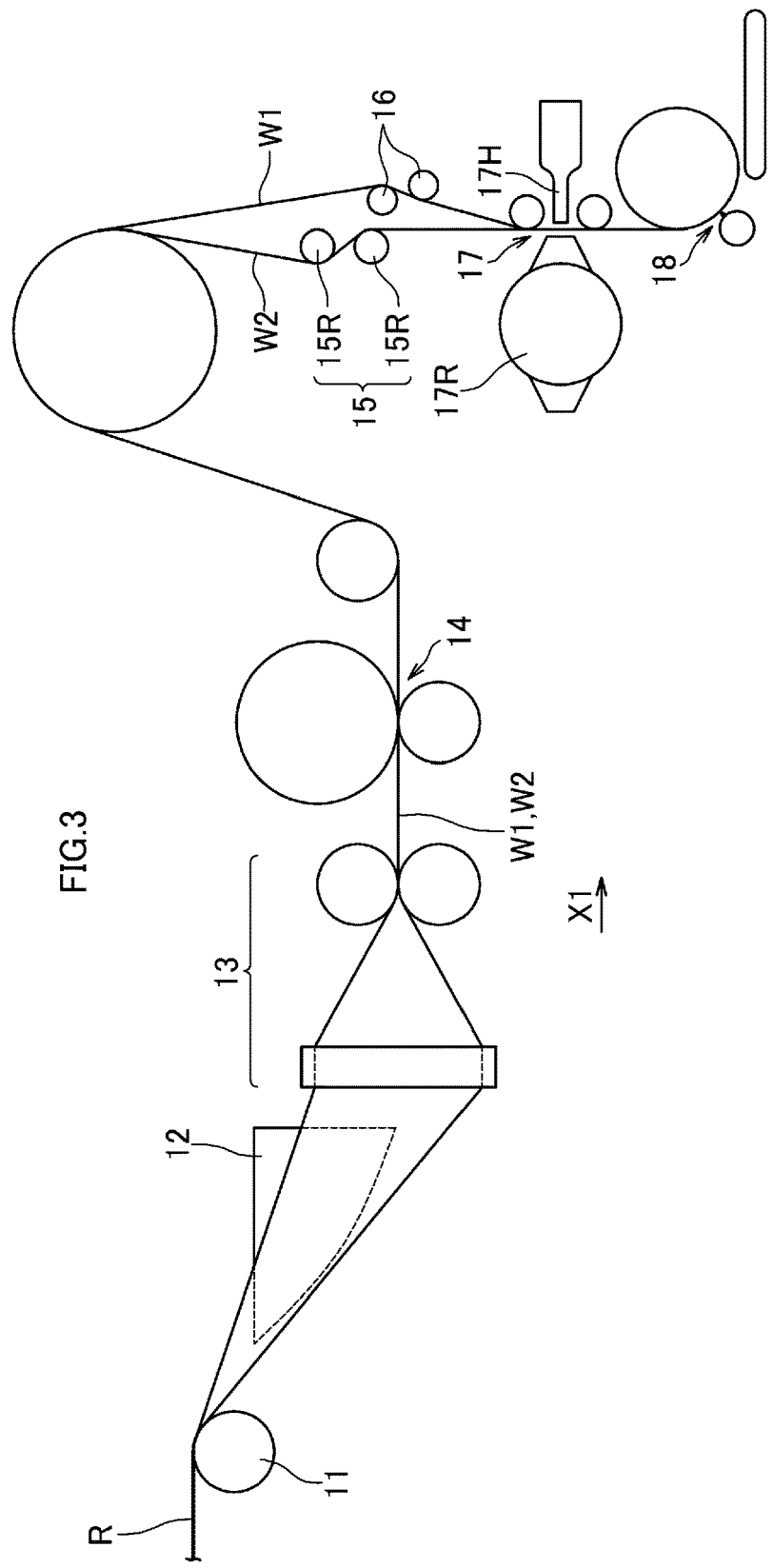

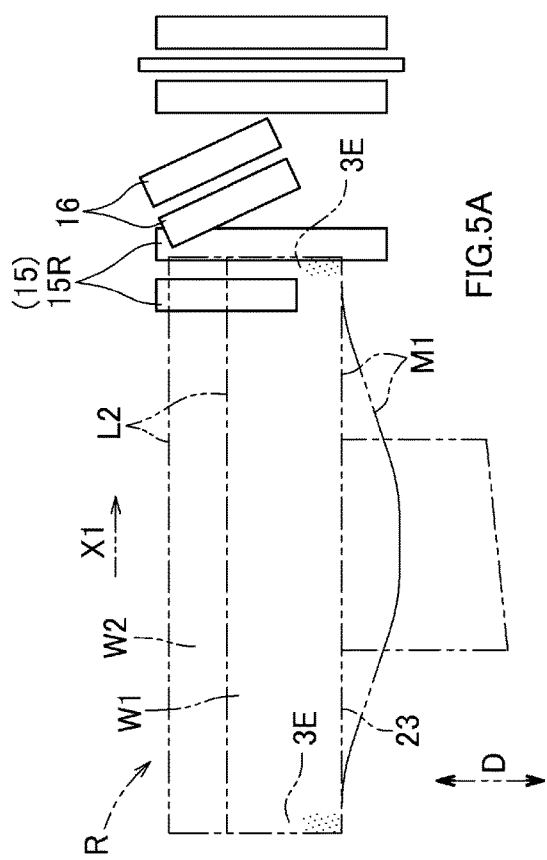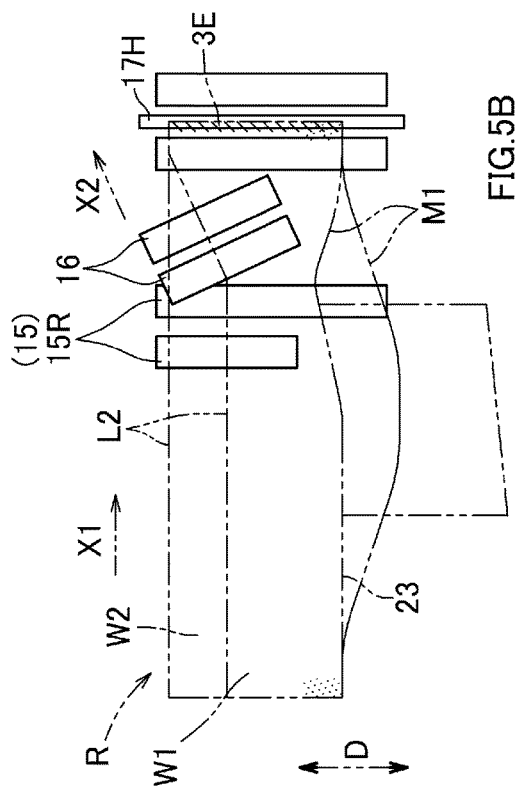

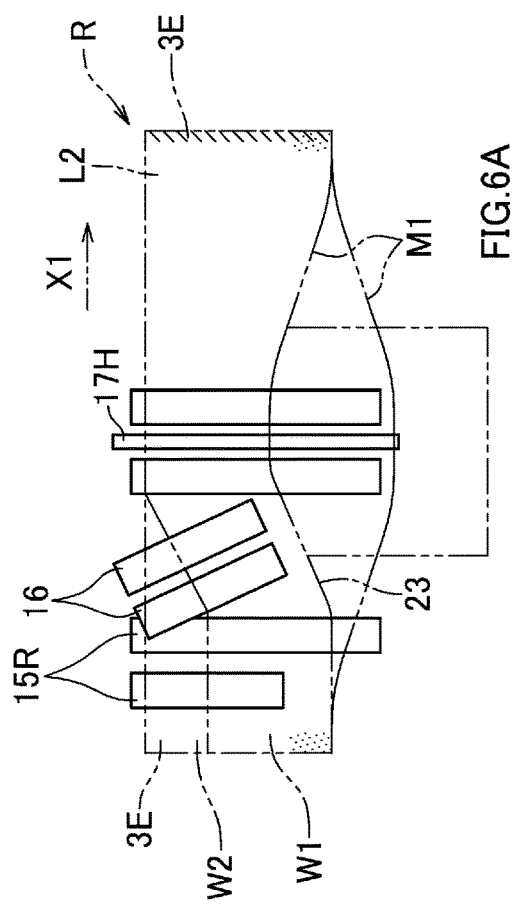
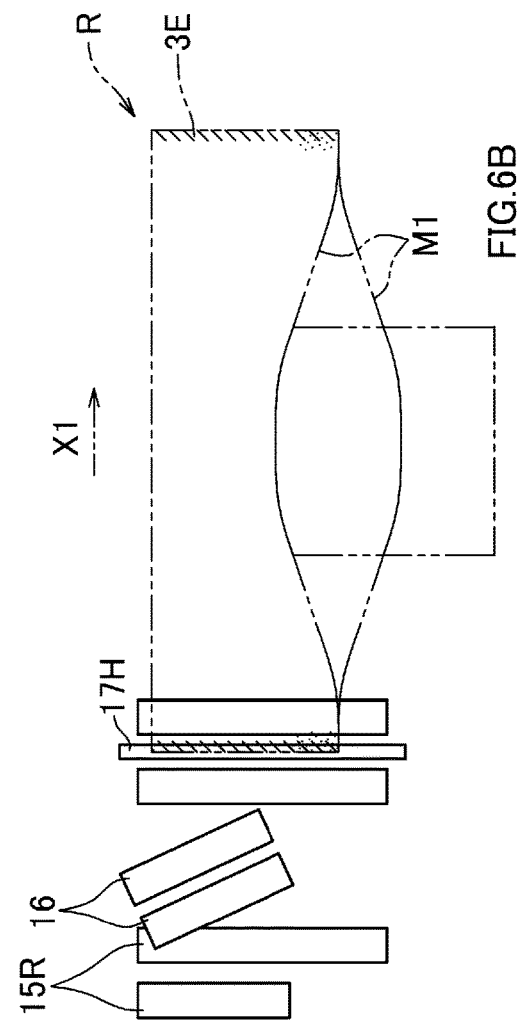

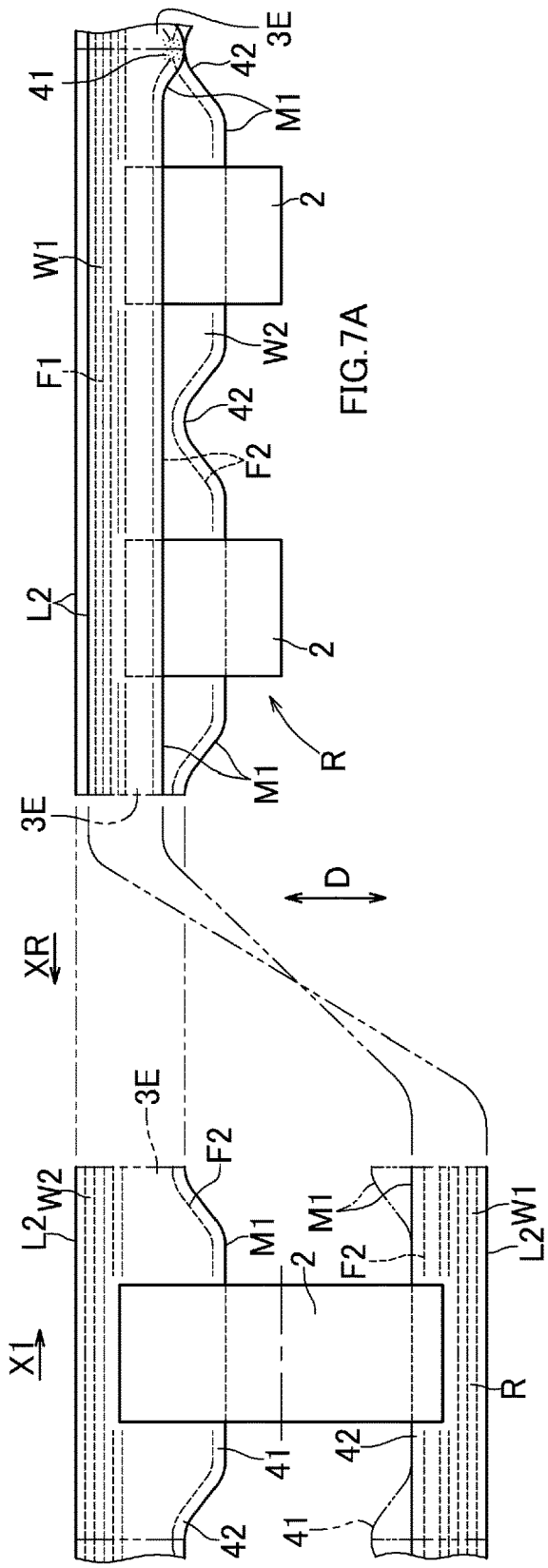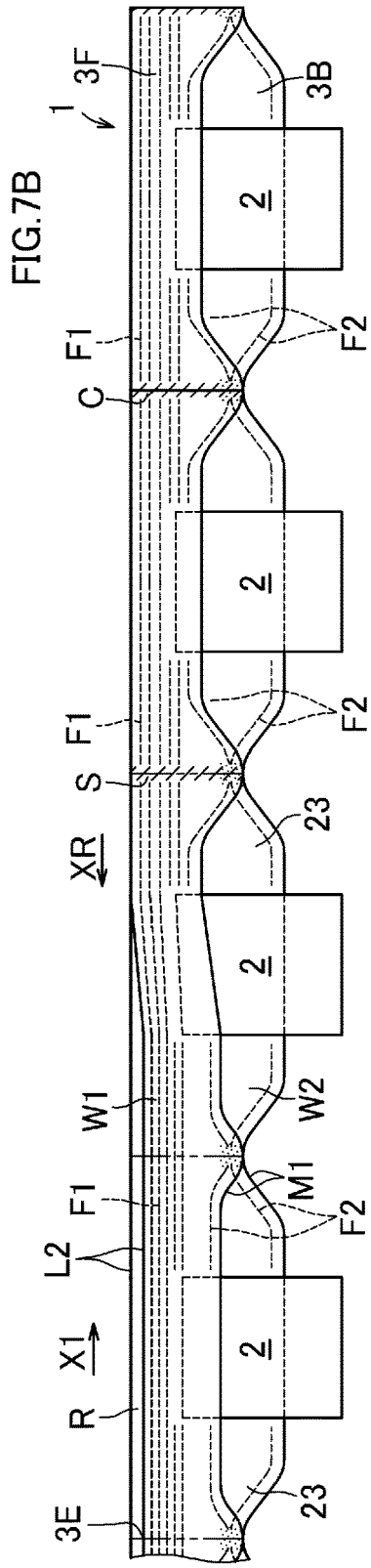

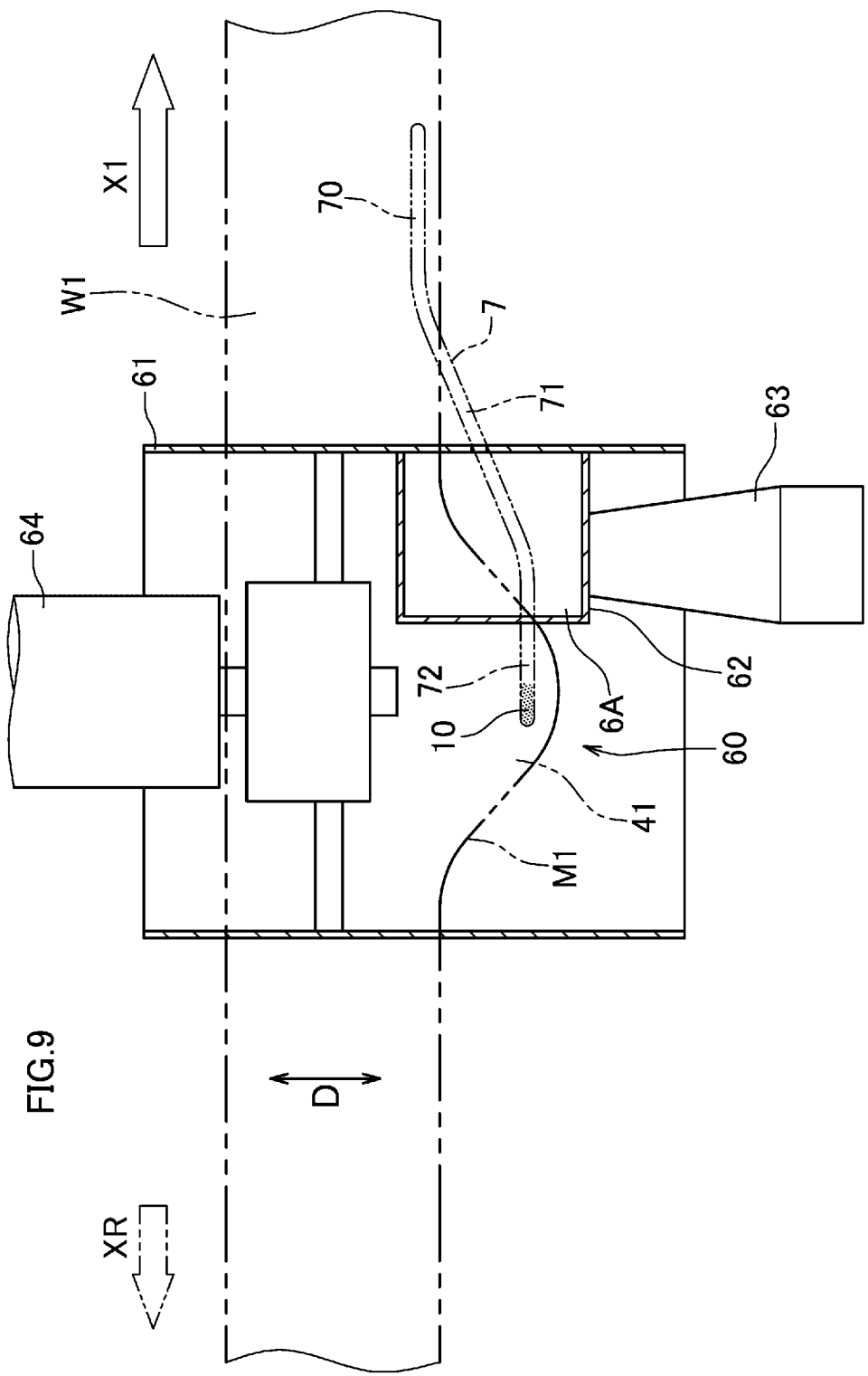

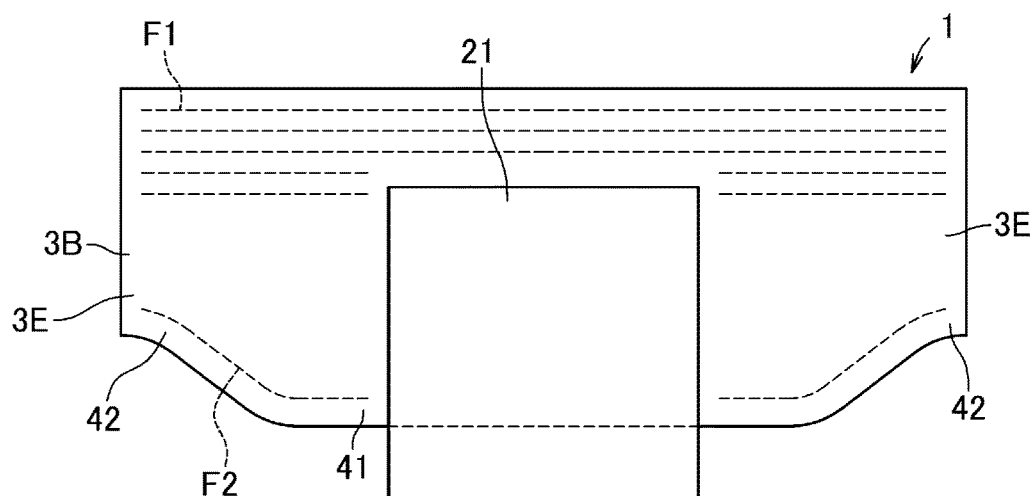
FIG.11A
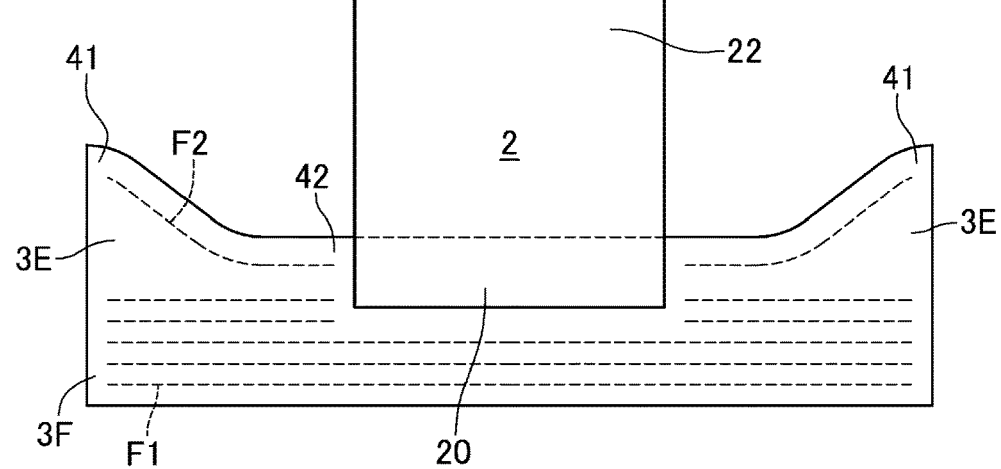
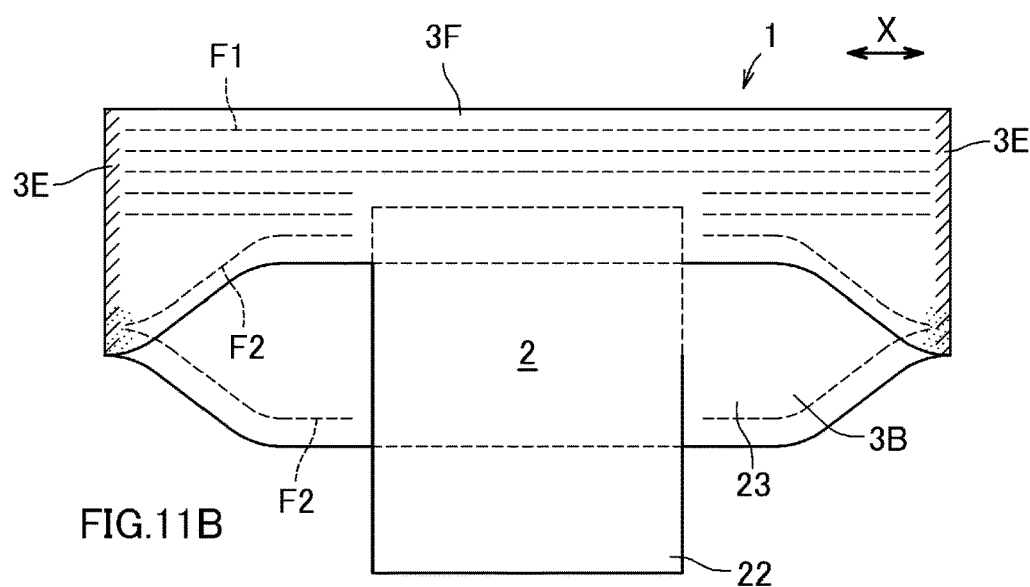
FIG.11B

METHOD AND DEVICE FOR MANUFACTURING WORN ARTICLE

TECHNICAL FIELD

The present invention relates to a method and a device for manufacturing a worn article, and more particularly to a device and a method for manufacturing a disposable worn article while carrying a web of the disposable worn article.

BACKGROUND ART

It is well known in the art that in the process of manufacturing disposable diapers, or the like, a continuous web is slit into two or three pieces along a wave-shaped severing line extending in the carrying direction.

CITATION LIST

Patent Literature

[First Patent Document] JP2002-272781A (Abstract)
[Second Patent Document] WO2005/013871A1 (Abstract)

SUMMARY OF INVENTION

However, divided webs obtained by slitting in a wave-shaped pattern have periodic protruding portions that protrude in the width direction perpendicular to the carrying direction. It is difficult to have these protruding portions under a tension in the carrying direction. Therefore, the shape of the protruding portions is likely to be unstable while being carried. Particularly, when an elastic member is placed extending along the edge of the protruding portion, the protruding portion is likely to be creased by the shrinking force of the elastic member. These creases make it difficult to attach, i.e., seal, together the opposite end portions of the worn article in the carrying direction. The creases also make it more likely that the front and back torso portions are misaligned with each other.

It is therefore an object of the present invention to provide a method and a device for manufacturing a worn article, with which the shape of a continuous web having protruding portions is likely to be stable, thus improving the quality of the seal made by attachment.

A method of the present invention is a method for manufacturing a worn article for producing individual worn articles from a continuous laminate, the continuous laminate including a first continuous web to be (become) one torso portion of each of the worn articles, a second continuous web to be (become) the other torso portion of each of the worn articles, and a plurality of absorbent bodies provided so as to bridge in a width direction between the first and second continuous webs, the method including:

a step of carrying the continuous laminate in a carrying direction extending along a direction in which the first and second continuous webs are continuous;

a step of folding, in two, the continuous laminate at each of the absorbent bodies so that the first continuous web and the second continuous web are laid on (superimposed, overlapped) each other;

a first attachment step, in which a portion of a first edge of the first continuous web and a portion of a first edge of the second continuous web are attached together intermittently in the carrying direction with the first and second continuous webs laid on each other, the first edges of the first and second continuous webs extending in the carrying direction and being to be leg holes of the worn article;

a step of smoothing out (straightening), in the width direction, creases on at least one of the first and second continuous webs after the first attachment step; and a second attachment step, in which the first continuous web and the second continuous web are attached together at least at portions of (along) second edges opposite to the first edges, with the creases being smoothed out (straightened).

A device of the present invention is a device for manufacturing individual worn articles from a continuous laminate, the continuous laminate including a first continuous web to be (become) one torso portion of each of the worn articles, a second continuous web to be (become) the other torso portion of each of the worn articles, and a plurality of absorbent bodies provided so as to bridge in a width direction between the first and second continuous webs, the device including:

a carrying device for carrying the continuous laminate in a first carrying direction extending along a direction in which the first and second continuous webs are continuous;

a folding device for folding, in two, the continuous laminate at each of the absorbent bodies so that the first continuous web and the second continuous web are laid on (superimposed, overlapped) each other;

a first attachment device, by which a portion of a first edge of the first continuous web and a portion of a first edge of the second continuous web are attached together intermittently in the first carrying direction with the first and second continuous webs laid on each other, the first edges of the first and second continuous webs extending in the first carrying direction and being to be leg holes of the worn article;

at least one inclined roller, placed on an inclined axis that is inclined with respect to a primary axis direction perpendicular to the first carrying direction, for straightening creases on at least one of the first and second continuous webs in the width direction; and a second attachment device, by which the first continuous web and the second continuous web are attached together at least at portions of (along) second edges opposite to the first edges, with the creases being smoothed out (straightened).

According to the present invention, it is possible to straighten, in the width direction, creases on the at least one continuous web in the straightening step between the first attachment step and the second attachment step, or in the step between the attachment by the first attachment device and the attachment by the second attachment device. This stabilizes the shape of the at least one continuous web, and makes it possible to attach the continuous webs together with no creases or small creases on the at least one continuous web. As a result, the quality of the seal obtained by the attachment will be improved and stable.

Note that there may be provided a plurality of inclined rollers.

BRIEF DESCRIPTION OF DRAWINGS

FIG. 2A and FIG. 2B are schematic plan views showing a method for manufacturing the worn article.

FIG. 3 is a layout diagram showing one embodiment of a manufacturing device.

FIG. 5A and FIG. 5B are conceptual plan views illustrating an important part of one embodiment of the manufacturing method.

FIG. 6A and FIG. 6B are conceptual plan views illustrating an important part of one embodiment of the manufacturing method.

FIG. 7A and FIG. 7B are conceptual diagrams showing a method for manufacturing a worn article according to another embodiment of the present invention.

FIG. 9 is a schematic cross-sectional view of the carrying device.

FIG. 11A and FIG. 11B are a developed view and a plan view, respectively, of the worn article.

DESCRIPTION OF EMBODIMENTS

Figure 1A:
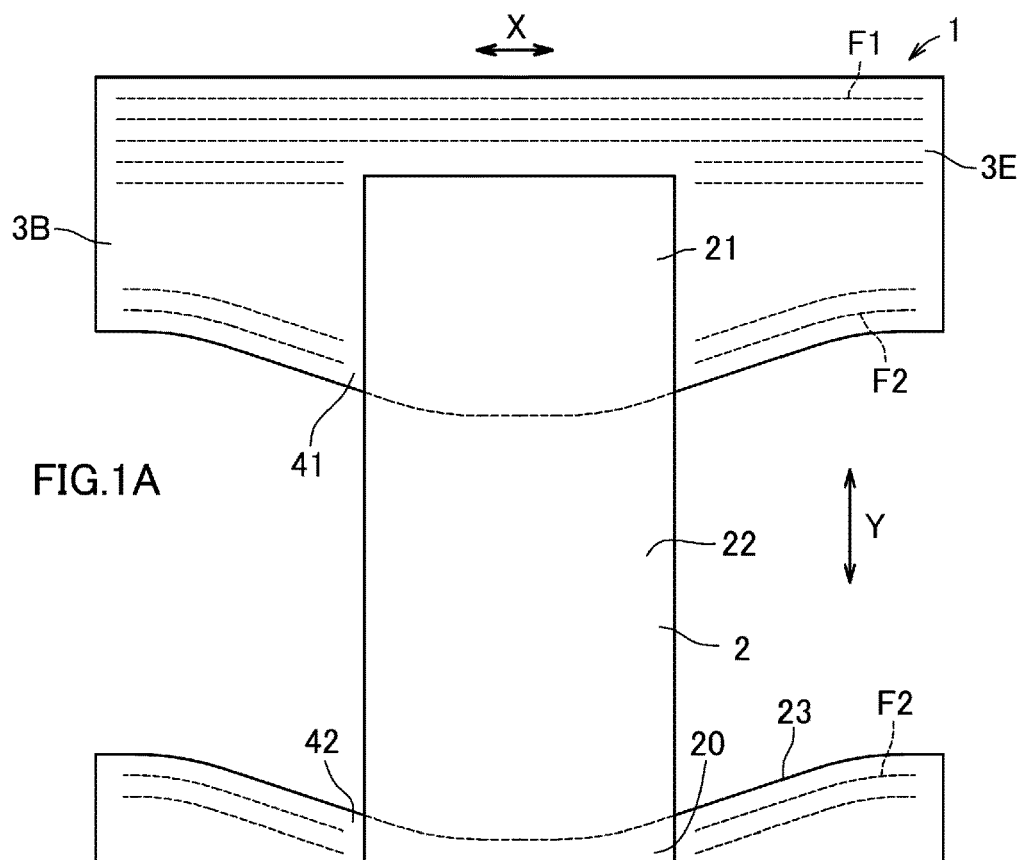
FIG. 1A and FIG. 1B are a developed view and a front view, respectively, showing an example worn article to which the present invention is applied.

Preferably, in the present manufacturing method, the absorbent body is folded in two so that the first edges are in a predetermined positional relationship with each other.

In this case, since folding in two is done so that the first edges are in a predetermined positional relationship, the shape of the attached portions is unlikely to vary. For example, the shape of the two sealed end portions of the worn article is unlikely to vary.

Preferably, in the present manufacturing method, in the second attachment step, the first continuous web and the second continuous web are attached together across an extent from the first edge to the second edge.

In this case, the opposite (both) end portions of the worn article can be sealed across the entire width.

Preferably, the present manufacturing method further includes a holding step of suppressing (reducing) or preventing a movement, in the width direction, of the portions of the first edges, which have been attached together in the first attachment step.

In this case, the portions of the first edges, which have been attached together in the first attachment step, are unlikely to move in the width direction. This enhances the reliability of the seal.

Preferably, the present manufacturing method further includes, after the step of folding in two and before the first attachment step, a step of previously smoothing out (straightening) creases on the one continuous web in the width direction, intended for portions of the one continuous web that are attached together in the first attachment step.

In this case, creases on portions that are attached together in the first attachment step are straightened in advance in the width direction. Thus, it is likely that there is realized an intended state of attachment or an intended force of attachment in the first attachment step.

Preferably, in the present manufacturing device, the inclined roller is placed so as to be in contact with the second edge of the torso portion of the one (first or second) continuous webs; and a second carrying direction of the inclined roller extends toward the second edge of the other (second or first) continuous web while extending downstream in the first carrying direction.

In this case, the one continuous web is carried in the second carrying direction so that the second edges of the two continuous webs are aligned together or close together.

More preferably, the present manufacturing device further includes a roller to be in contact with the other (second or first) continuous web so as to provide the same distance increase to a carrying path of the other continuous web as an increase to a carrying distance of the one (first or second) continuous web that is incurred by being carried in contact with the inclined roller.

In this case, the two continuous webs in the carrying direction will be an intended phase. Thus, it is possible to prevent misalignment between the continuous webs in the carrying direction.

Preferably, the present manufacturing device further includes a holding device for suppressing (reducing) or preventing a movement, in the width direction, of the portions of the first edges, which have been attached together by the first attachment device.

In this case, portions of the first edges, which have been attached together by the first attachment device, are unlikely to move in the width direction.

Preferably, the present manufacturing device further includes a crease smoothing-out (straightening) device for smoothing out (straightening), in advance of attachment by the first attachment device, creases on portions of the first edges in the width direction, which will be attached together by the first attachment device.

In this case, creases on portions that are attached together in the first attachment device are straightened in advance in the width direction by the crease smoothing-out (straightening) device. Therefore, an intended state of attachment or an intended force of attachment is likely to be realized on the portions of the first edges that are to be attached together by the first attachment device.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Prior to the description of embodiments of the present invention, an example structure of a worn article 1 will be described with reference to the drawings.

As shown in the developed view of FIG. 1A, the worn article 1 includes an absorbent body 2, and a pair of (front and back) around-torso members 3F and 3B. The absorbent body 2 includes a front portion (torso portion) 20, a back portion (torso portion) 21, and a crotch portion 22. The front portion 20 extends in the girth direction X covering the front torso of the wearer. The back portion 21 extends in the girth direction X covering the back torso of the wearer. The crotch portion 22 covers the crotch of the wearer between the front portion 20 and the back portion 21.

The crotch portion 22 is continuous with the front portion 20 and the back portion 21, and extends in a longitudinal direction Y perpendicular to the girth direction X. The absorbent body 2 forms a part or whole of the crotch portion 22.

Figure 1B:
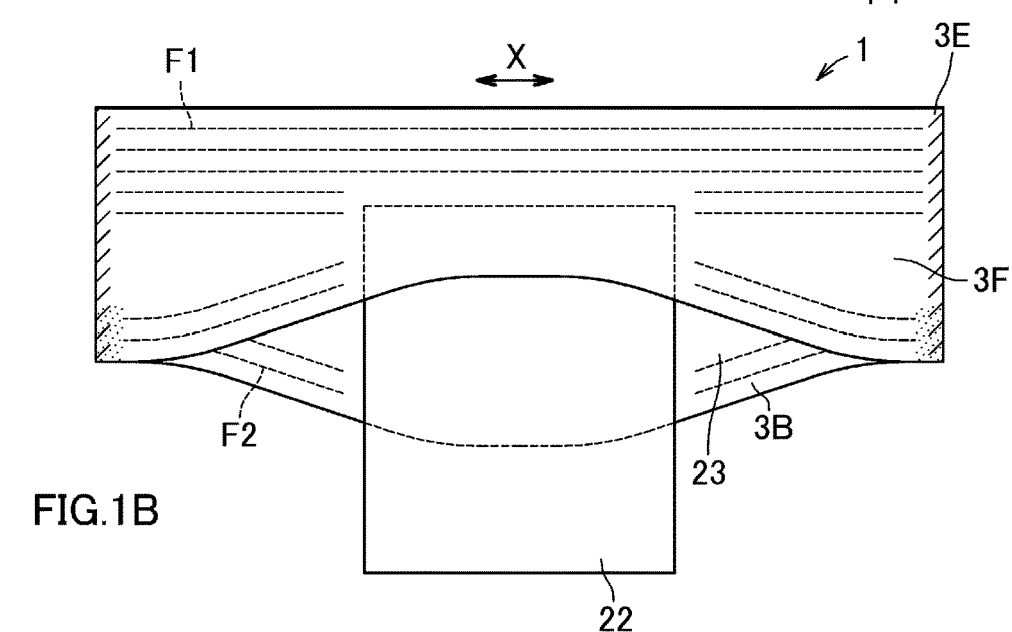

As shown in FIG. 1B, the present worn article 1 is worn while the crotch portion 22 is folded in two along a virtual line parallel to the girth direction X. That is, the end portions 3E in the girth direction X of the front around-torso member 3F and those of the back around-torso member 3B are sealed together while they are laid on each other. The present worn article is a pants-type worn article, and the end portions in the girth direction X of the front portion 20 and those of the back portion 21 may be welded together.

An absorbent core (not shown) may be provided in the absorbent body 2. A cuff may be provided on a top sheet (not shown) covering the skin-contact surface of the absorbent core.

As shown in FIG. 1A, the absorbent body 2 is placed so as to bridge between the front around-torso member 3F and the back around-torso member 3B. That is, the front portion 20, which is one end portion in the longitudinal direction Y of the absorbent body 2, is bonded to the front around-torso member 3F. On the other hand, the back portion 21, which is the other end portion in the longitudinal direction Y of the absorbent body 2, is bonded to the back around-torso member 3B.

The front around-torso member 3F includes a depressed portion 42 in the central portion in the girth direction X where the absorbent body 2 is laid thereon. On the other hand, the back around-torso member 3B includes a protruding portion 41 in the central portion in the girth direction X where the absorbent body 2 is laid thereon. The respective opposite end portions 3E of the around-torso members 3F and 3B are set to have the same height (width).

Each around-torso members 3F and 3B may be formed from a laminate including a torso elastic member F1 and a leg elastic member F2 sandwiched between a pair of webs (only one web is shown in the figure).

The elastic members F1 and F2 are sandwiched between the pair of webs, and are stretchable in the girth direction X. The elastic members F1 and F2 may be cut off in the areas of the around-torso members 3F and 3B where the front portion 20 and the back portion 21 of the absorbent body 2 are placed.

Next, prior to the description of the present manufacturing method, an example of the present manufacturing device will be described.

The present manufacturing device produces worn articles 1 (FIG. 1B) from a continuous laminate R that includes a first continuous web W1 of FIG. 2 to be one torso portion of an individual worn article 1 of FIG. 1B, a second continuous web W2 to be the other torso portion of the worn article, and a plurality of absorbent bodies 2 provided so as to bridge in the width direction D between the first and second webs W1 and W2.

As shown in FIG. 3, the present manufacturing device includes a carrying device 11, a folding device 12, a twisting device 13, a first attachment device 14, a holding device 15, an inclined roller 16, a second attachment device 17, a severing device 18, etc. The carrying device 11 includes a power source such as a motor (not shown) and a drive roller and many rollers for carrying the continuous laminate R in the first carrying direction X1, which extends along the direction in which the first and second continuous webs W1 and W2 are continuous of FIG. 2A and FIG. 2B.

The folding device 12 of FIG. 3 includes a sailor, for example, for folding the continuous laminate R in two at the absorbent body 2 so that the first continuous web W1 and the second continuous web W2 are laid on each other as shown in FIG. 2A. That is, the continuous laminate R is folded in two along the virtual folding line L extending in the first carrying direction X1.

In this process, the first and second webs W1 and W2 are folded in two while being positioned so as to align the positions of first edges M1 and M1 of the webs forming the leg hole 23 in the central portion between adjacent absorbent bodies 2 and 2.

The twisting device 13 of FIG. 3 twists the two-folded continuous laminate R by 90° so that the continuous laminate R is carried along a horizontal plane.

Note that the twisting device 13 may be formed by an array of many pairs of rollers or pairs of conveyor belts.

As shown in FIG. 2B, portions of the first edges M1, extending in the first carrying direction X1 of the first and second webs W1 and W2 laid on each other, to be the leg hole 23 of the worn article are attached together intermittently in the first carrying direction X1 by the first attachment device 14.

The attachment may be a tentative attachment, and a heat seal device, for example, may be used as the first attachment device 14.

Note that in FIG. 1B, FIG. 2A and FIG. 2B, the attached portions are dotted.

Figure 4B:
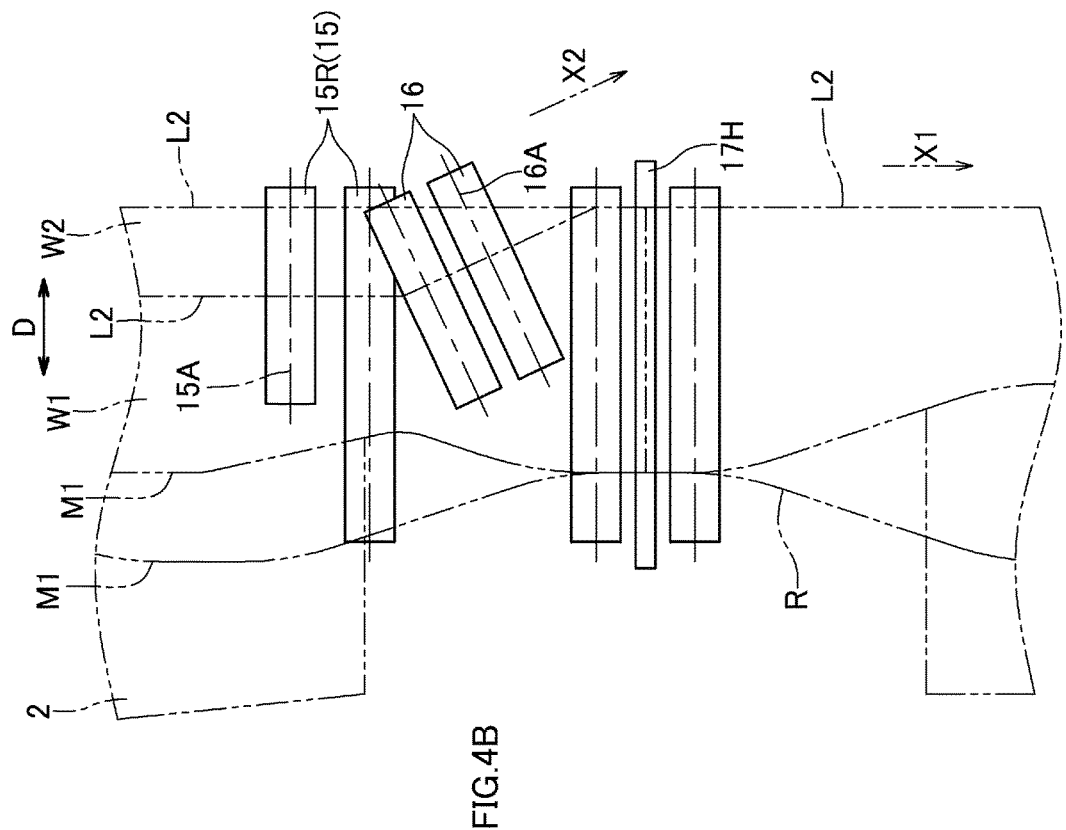
FIG. 4A and FIG. 4B are a layout diagram and a conceptual plan view, respectively, showing an important part of one embodiment of the device.
Figure 4A:
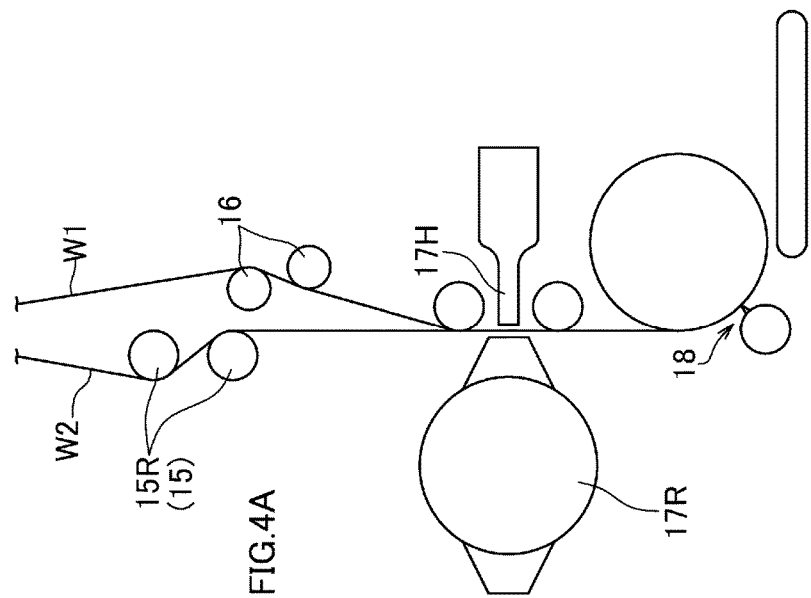

As shown in FIG. 3, FIG. 4A and FIG. 4B, the holding device 15 and the inclined rollers 16 come into contact with the second and first webs W2 and W1, respectively, being carried separately in two directions.

Note that in FIG. 4B, the continuous laminate R is indicated by a two-dot chain line.

In the present embodiment, as shown in FIG. 4B, the two inclined rollers 16 are placed on inclined axes 16A that are parallel to each other and inclined with respect to a primary axis 15A perpendicular to the first carrying direction X1 in order to straighten creases on the first continuous web W1 in the width direction D.

The inclined rollers 16 are placed so as to be not in contact with the first edge M1 and in contact with a second edge L2 of the torso portion of the first continuous web W1. The inclination of the inclined axes 16A of the inclined rollers 16 is set so that the second carrying direction X2 of the inclined rollers 16 extends toward the second edge L2 of the second continuous web W2 while extending downstream in the first carrying direction X1.

Note that there may be one inclined roller 16 or three or more inclined rollers 16. When there are a plurality of inclined rollers 16, they do not need to be parallel to each other as long as they are inclined in the same direction.

As shown in FIG. 3, the holding device 15 may include a pair of hold rollers 15R and 15R for reducing or preventing the movement in the width direction D (FIG. 2) of portions of the first edges M1 of the first and second webs W1 and W2, which have been attached together by the first attachment device 14.

The pair of hold rollers 15R are in contact with the second continuous web W2 so as to provide the same distance increase to the carrying path of the second continuous web W2 as the increase to the carrying distance of the first continuous web W1 that is incurred by being carried in contact with the inclined rollers 16 and 16.

Note that as shown in FIG. 4B, the pair of hold rollers 15R and 15R extend in parallel to each other and along the primary axes 15A.

The second attachment device 17 of FIG. 3 may be an ultrasonic welding device including an anvil roll 17R and an ultrasonic horn 17H, for example.

The second attachment device 17 may attach the first continuous web W1 and the second continuous web W2 to each other at least at portions along the second edge L2, opposite to the first edge M1, of FIG. 2B, with creases on the first continuous web W1 being straightened.

In the present embodiment, as shown in FIG. 2B, the first continuous web W1 and the second continuous web W2 are attached together at a seal portion S across the entire width from the first edge M1 to the second edge L2.

The severing device 18 of FIG. 3 successively severs the continuous laminate R along the severing line C at the seal portion S of FIG. 2B at which the webs have been attached by the second attachment device 17 to thereby obtain individual diapers. The severing device 18 includes a cutter and an anvil, for example.

Note that this severing may be performed at the same time with the welding by the ultrasonic horn 17H.

Next, an example manufacturing method will be described.

As shown in FIG. 2A, the absorbent bodies 2 are successively provided so as to bridge in the width direction D between the first continuous web W1 and the second continuous web W2, thus producing the continuous laminate R. The folding step, the first attachment step, the straightening step, the second attachment step and the severing step to be described below are performed while the continuous laminate R is carried in the first carrying direction X1, which extends along the direction in which the first and second webs W1 and W2 are continuous.

In the folding step, the continuous laminate R is folded in two at the absorbent body 2 by the folding device 12 of FIG. 3 so that the first continuous web W1 and the second continuous web W2 of FIG. 2A are laid on each other. In the folding step, the absorbent body 2 is folded in two at the central portion between adjacent absorbent bodies 2 and 2 so that the webs W1 and W2 are laid on each other.

Due particularly to the tension from the elastic member F2, the first continuous web W1 is creased in protruding portions of the first continuous web W1, thereby shrinking the first continuous web W1 in the width direction D. On the other hand, the protruding portion 41 of the second continuous web W2 of the present embodiment is not creased because the absorbent body 2 is placed thereon. On the other hand, since the depressed portion of the second continuous web W2 is under a tension in the carrying direction, it is unlikely shrunk in the width direction D. Therefore, when the continuous laminate R is folded so that the first edges M1 of the first and second webs W1 and W2 are laid on each other at portions in the central portion between adjacent absorbent bodies 2 and 2, the second edges L2 of the continuous webs W1 and W2 are misaligned with each other.

That is, when the continuous laminate R is folded so that the first edges M1 of the first and second webs W1 and W2 are laid on each other at portions in the central portion between adjacent absorbent bodies 2 and 2, with the first continuous web W1 being shrunk in the width direction D, the second edges L2 of the continuous webs W1 and W2 will be misaligned with each other in the width direction D.

In the first attachment step, at each position to be the end portion 3E of an individual worn article 1, the first edges M1 to be the leg hole 23 of the worn article 1 are attached together intermittently in the first carrying direction X1, as indicated by dotted portions, by the first attachment device 14 (FIG. 3).

Then, the second edge L2 of the first continuous web W1 of the continuous laminate R is carried while being in contact with the two inclined rollers 16 of FIG. 3. On the other hand, the second edge L2 of the second continuous web W2 of the continuous laminate R of FIG. 2B is carried while being in contact with the two hold rollers 15R of FIG. 3.

In FIG. 5A to FIG. 6B, individual diaper portions of the continuous laminate R are indicated by a two-dot chain line.

As shown in FIG. 5A to FIG. 6A, the holding step of reducing or preventing the movement in the width direction D of portions of the first edges M1, which have been attached together in the first attachment step, is performed as the second continuous web W2 of the continuous laminate R passes through between the pair of hold rollers 15R.

In the straightening step, the first continuous web W1 of the continuous laminate R of FIG. 5A come into contact with a pair of inclined rollers 16 as shown in FIG. 4A and FIG. 5B, thereby straightening creases on the first continuous web W1 in the width direction D.

That is, the second edge L2 of the first continuous web W1 carried in the first carrying direction X1 of FIG. 5A comes into contact with the inclined rollers 16 inclined with respect to the first carrying direction X1. Upon contact, the second edge L2 of the first continuous web W1 is carried, along the rotation direction of the inclined rollers 16 of FIG. 5B, in the second carrying direction X2 that extends toward the second edge L2 of the second continuous web W2.

The inclined rollers 16 come into contact with the second edge L2 of the first continuous web W1 but not with the first edge M1. Therefore, the inclined rollers 16 stretch the second edge L2 of the first continuous web W1 in the width direction D, thereby preventing the absorbent body 2 on the leg hole 23 side from interferring with the inclined rollers 16 even when the first continuous web W1 is continuously in contact with the inclined rollers 16.

The portions of the first edges M1 of the first continuous web W1 that have been attached together in the first attachment step are held by the hold rollers 15R with the second continuous web W2 therebetween, and the portions are prevented from being carried in the second carrying direction X2. That is, in the central portion between adjacent absorbent bodies 2 and 2, the first edge M1 of the first continuous web W1 is not carried in the second carrying direction X2 but carried in the first carrying direction X1, and the second edge L2 of the web W1 is carried in the carrying direction X2.

As the second edge L2 of the first continuous web W1 is carried in the second carrying direction X2, there is a crease-straightening force acting upon the second edge L2 of the first continuous web W1. Then, in the central portion between adjacent absorbent bodies 2 and 2, the portions of the continuous laminate R to be the end portions 3E are laid on each other across the entire extent in the width direction D, with the second edges L2 of the continuous webs W1 and W2 aligned with each other.

That is, in the central portion between adjacent absorbent bodies 2 and 2, the first edges M1 of the first and second webs W1 and W2 are carried in the first carrying direction X1 without moving in the width direction D. On the other hand, the second edge L2 of the first continuous web W1 is carried in the second carrying direction X2, thereby straightening creases on the first continuous web W1 in the width direction D so that the width of the first continuous web W1 becomes equal to the width of the second continuous web W2 at the end portion 3E.

In the second attachment step, the first continuous web W1 and the second continuous web W2 are attached together at least at portions along the second edges L2 opposite to the first edges M1, with the creases being straightened.

In the present embodiment, as shown in FIG. 5B, the first continuous web W1 and the second continuous web W2 are attached together, across the extent from the first edge M1 to the second edge L2, along one of the two end portions 3E (one end portion).

While the second attachment step is performed intermittently, the straightening step continues to be performed also before the second attachment step, simultaneously with the second attachment step, and after the second attachment step as shown in FIG. 6A. Then, as shown in FIG. 6B, when the other one of the end portions 3E (the other end portion) reaches the horn 17H, the portion is ultrasonically welded.

The straightening step of the present embodiment may be performed not by the inclined rollers 16, but by contact with a roller, a ball or an endless belt rotating in the width direction D extending toward the second edge L2, for example. When the two continuous webs W1 and W2 are both creased, the continuous webs W1 and W2 may be stretched individually.

Next, another embodiment of the present invention will be described with reference to FIG. 7A to FIG. 11B.

Prior to the description of the carrying method and the carrying device, the structure of the diaper of the present embodiment will be described.

Referring to FIG. 11A and FIG. 11B, in the present embodiment, the absorbent body 2 is placed so as to bridge between the depressed portion 42 of a front around-torso member 3F and the protruding portion 41 of a back around-torso member 3B. On the other hand, as shown in the developed view of FIG. 11A and in FIG. 11B, the front and back around-torso members 3F and 3B may be of the same height (width) at the opposite end portions 3E and 3E thereof along which the front and back around-torso members 3F and 3B are sealed together.

That is, the opposite end portions 3E of the front around-torso member 3F of FIG. 11A are formed by the protruding portion 41, and the opposite end portions 3E of the back around-torso member 3B are formed by the depressed portion 42.

Next, the carrying device will be described.

Figure 8:
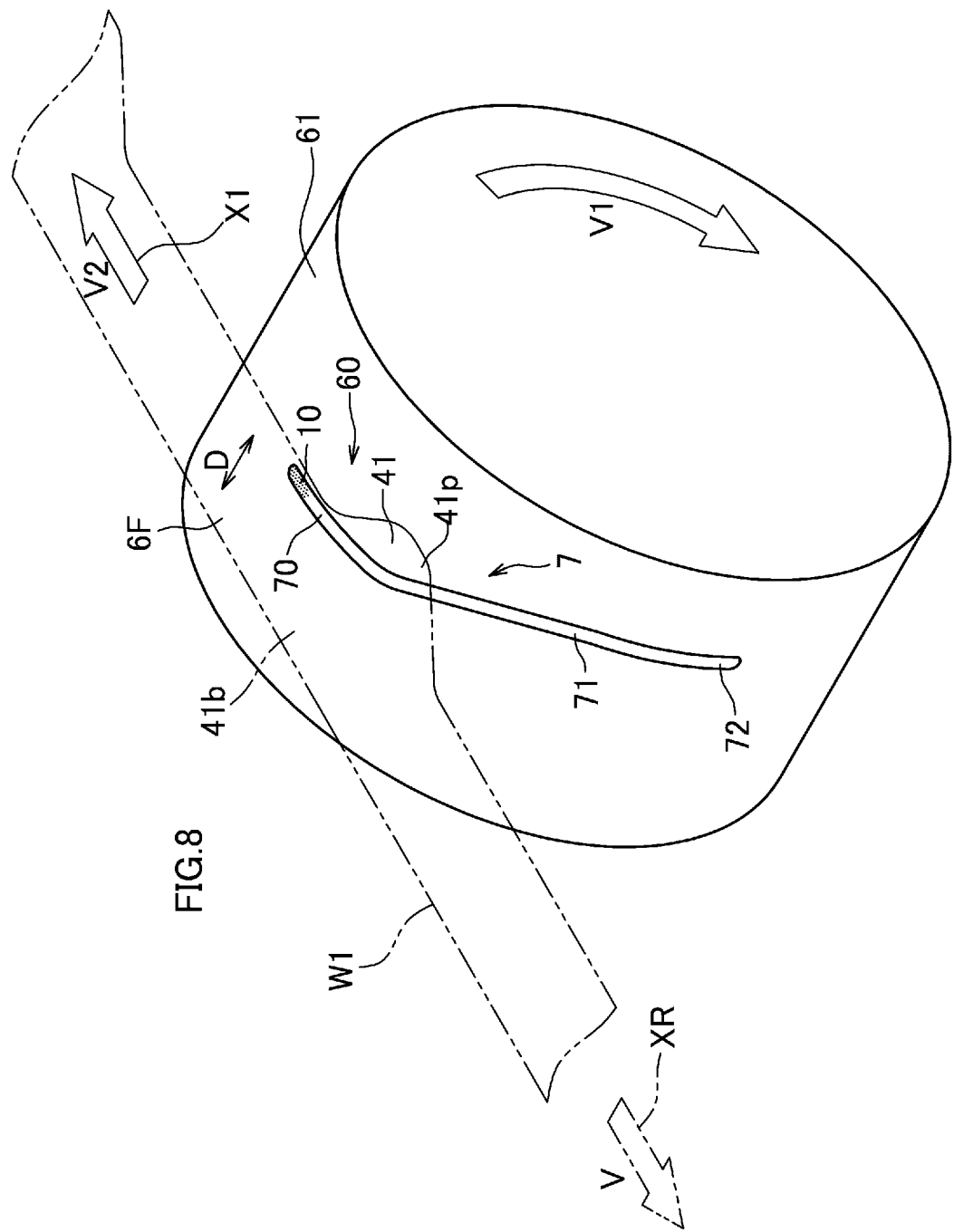
FIG. 8 is a schematic perspective view showing a part of the carrying device.

As shown in FIG. 8, the present carrying section 61 is a drum, forming a part of a crease straightening device 60. As shown in FIG. 9, the present carrying section 61 rotates at the circumferential velocity V as shown in FIG. 8 by the driving force from a drive shaft 64. The tangential direction of the circumferential velocity V is equal to the direction of the carrying velocity V2 of the first continuous web W1, and the circumferential velocity V is greater than the carrying velocity V2. Therefore, the direction XR of the relative velocity V (relative direction) of the first continuous web W1 with respect to the contact surface 6F of the carrying section 61 is opposite to the actual carrying direction (the first carrying direction) X1, as indicated by a phantom line.

Note that the first continuous web W1 contacts the contact surface 6F approximately in a linear contact.

As shown in FIG. 9, the carrying section 61 is formed by a hollow cylinder. The box 62 and a duct as the suction pipe 63 are placed inside the carrying section 61. The box 62 and the suction pipe 63 may not be rotatable but be secured to a frame (not shown).

Note that in FIG. 9, the slit 7 is shown as being developed and is indicated by a two-dot chain line.

In the present embodiment, the slit 7 of FIG. 8 forms a part of the crease straightening device 60 and is formed on the cylinder (drum). The slit 7 extends in an inclined direction so as to be displaced from the proximal side 41b toward the distal side 41p of the protruding portion 41 while extending in the relative direction XR in which it travels relative to the contact surface 6F of the first continuous web W1.

Next, an example of a manufacturing method will be described with reference to FIG. 7.

First, as in the above-described embodiment, the absorbent bodies 2 are placed successively so as to bridge in the width direction D between the first continuous web W1 and the second continuous web W2, thus producing the continuous laminate R. The folding step, the first crease straightening step, the first attachment step, the second crease straightening step, the second attachment step and the severing step to be described below are performed while the continuous laminate R is carried in the first carrying direction X1, which extends along the direction in which the first and second continuous webs W1 and W2 are continuous.

In the folding step, the continuous laminate R is folded, at the absorbent body 2, in two so that the first continuous web W1 and the second continuous web W2 are laid on each other.

Due to the protruding shapes/depressed shapes and the tension from the elastic member F2 formed on the first continuous web W1, the first continuous web W1 is creased, and the protruding portion 41 of the first continuous web W1 indicated by a two-dot chain line is therefore shrunk significantly in the width direction D as indicated by a solid line. Therefore, the folding is performed while the first edges M1 of the pair of continuous webs W1 and W2 are misaligned with each other at the central portion between adjacent absorbent bodies 2 and 2, i.e., at a position to be the end portion 3E of each worn article.

As the protruding portion 41 is shrunk in the width direction D, the first continuous web W1 is shrunk in the width direction D. Therefore, the folding is performed while the second edges L2 of the pair of continuous webs W1 and W2 are misaligned with each other.

Thus, immediately after the folding in two, the edges are misaligned both on the waist side and on the leg hole side.

On the other hand, a negative pressure is acting along the slit 7 of FIG. 8 and FIG. 9 via the suction space 6A. Due to this negative pressure, the sucked portion 10 of the first edge M1 of the first continuous web W1 is sucked into the slit 7 with a sucking force that is greater than the force by which the protruding portion 41 is shrunk in the width direction D, while the first continuous web W1 is carried. Due to this suction, the protruding portion 41, which has been shrunk, is stretched as will be described below.

Figure 10A:
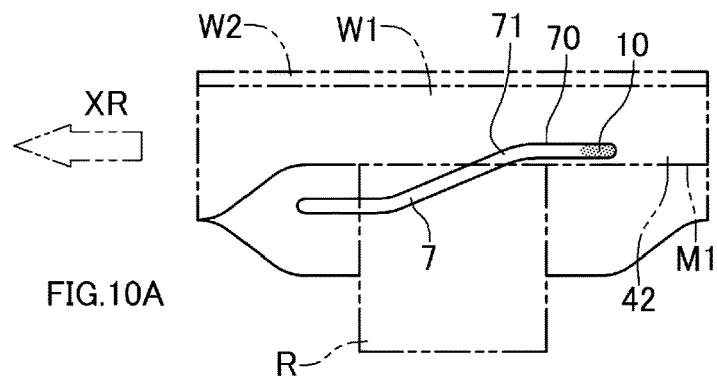
FIG. 10A, FIG. 10B, FIG. 10C and FIG. 10D are developed views showing how creases are straightened by the carrying device.

As shown in FIG. 10A, when the depressed portion 42 of the continuous web W1 reaches the upstream slit portion 70, the sucked portion 10 of the first edge M1 of the depressed portion 42 is sucked into and held against the slit 7 via the upstream slit portion 70.

Note that in FIG. 8 to FIG. 10, the sucked portion 10, being sucked into the slit 7, is dotted.

Then, when the protruding portion 41 of the first continuous web W1, being shrunk in the width direction D, reaches the upstream slit portion 70, the sucked portion 10 of the first edge M1 of the protruding portion 41 is sucked into and held against the upstream slit portion 70, with the sucked portion 10 being slightly inside the upstream slit portion 70.

Figure 10B:
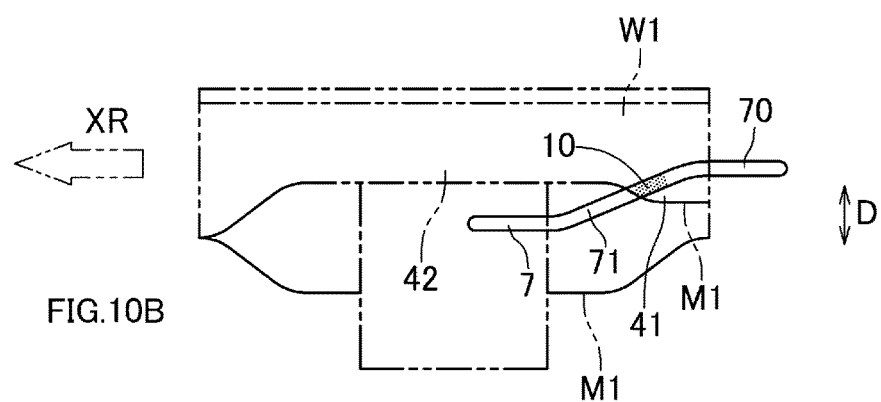

As shown in FIG. 10B, when the depressed portion 42 of the first continuous web W1 moves past the upstream slit portion 70 and reaches the inclined slit portion 71, the position of the depressed portion 42, which has been held against the slit 7, comes off the slit 7 and off the contact surface 6F of the carrying section 61 of FIG. 8.

Figure 10C:
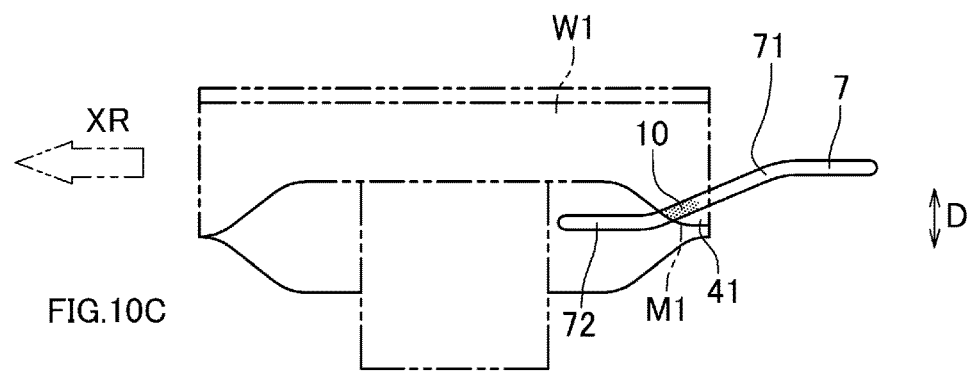
Figure 10D:
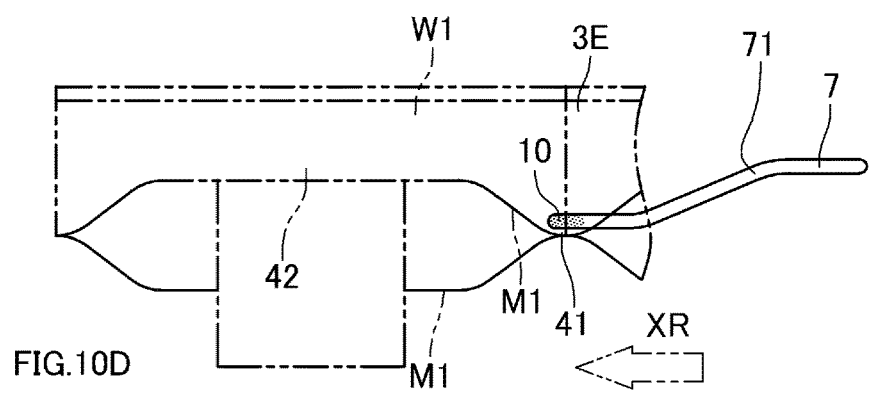

Then, as shown in FIG. 10C, as the first continuous web W1 is carried, the protruding portion 41 moves past the inclined slit portion 71. The portion that has moved past the inclined slit portion 71 comes off the inclined slit portion 71 and off the contact surface 6F of the carrying section 61 of FIG. 8. At this point, the portion of the first continuous web W1, which is held against the inclined slit portion 71 of FIG. 10C, is displaced in the width direction D, thereby stretching the protruding portion 41 in the width direction D perpendicular to the relative direction XR of FIG. 10D.

Referring to FIG. 7B, in the first attachment step, after the stretching, the continuous webs W1 and W2 are attached together intermittently in the first carrying direction X1, as indicated by dotting, at the position to be the end portion 3E of each worn article and at the first edges M1 to be leg holes 23 of the worn article 1.

Then, the second edge L2 of the first continuous web W1 of the continuous laminate R is carried while being in contact with the inclined rollers (not shown). On the other hand, the second edge L2 of the second continuous web W2 of the continuous laminate R is carried while being in contact with the hold rollers (not shown). Therefore, in the second crease straightening step, the second edge L2 of the first continuous web W1 is carried in an inclined direction by the inclined rollers, straightening the creases on the first continuous web W1 in the width direction D. Thus, the second edges L2 of the continuous webs W1 and W2 are aligned together or close together.

In the second attachment step, with the creases being straightened, the first continuous web W1 and the second continuous web W2 are attached successively at different positions, along one of the end portions 3E (one end), across the extent from the first edge M1 to the second edge L2.

After or during the attachment, the continuous laminate R may be severed into individual pairs of pants.

Note that the first and second attachment steps may each be performed by either heat seal or ultrasonic seal.

While preferred embodiments have been described above with reference to the drawings, various obvious changes and modifications will readily occur to those skilled in the art upon reading the present specification.

For example, no elastic members may be provided on worn articles manufactured by the present manufacturing method.

The continuous webs do not need to be laminates.

The web on which creases are straightened may be a web whose edge with no protruding portions/depressed portions extends in parallel to the carrying direction.

Thus, such variations and modifications shall fall within the scope of the present invention as defined by the appended claims.

INDUSTRIAL APPLICABILITY

The present invention is applicable to a disposable worn article such as a diaper, pants, a feminine sanitary product or a mask.

REFERENCE SIGNS LIST

1: Worn article
11: Carrying device, 12: Folding device, 13: Twisting device, 14: First attachment device, 15: Holding device, 15A: Primary axis, 16: Inclined roller, 16A: Inclined axis, 17: Second attachment device, 18: Severing device
2: Absorbent body, 20: Front portion, 21: Back portion, 22: Crotch portion, 23: Leg hole
3B: Back around-torso member, 3F: Front around-torso member, 3E: End portion
F1: Torso elastic member, F2: Leg elastic member
41: Protruding portion, 42: Depressed portion
60: Crease straightening device
C: Severing line, S: Seal portion, X: Girth direction, X1: First carrying direction, X2: Second carrying direction, XR: Relative direction, D: Width direction, Y Longitudinal direction
L2: Second edge
M1: First edge
R: Continuous laminate, W1: First continuous web, W2: Second continuous web

The invention claimed is:

1. A method for manufacturing a worn article by producing individual worn articles from a continuous laminate, the continuous laminate including a first continuous web to be one torso portion of each of the individual worn articles, a second continuous web to be another torso portion of each of the individual worn articles, and a plurality of absorbent bodies provided so as to bridge in a width direction between the first continuous web and the second continuous web, the method comprising:
   a step of carrying the continuous laminate in a carrying direction extending along a direction in which the first continuous web and the second continuous web are continuous;
   a step of folding, in two, the continuous laminate at each of the absorbent bodies so that the first continuous web and the second continuous web are laid on each other;
   a first attachment step, in which portions of respective first edges of the first continuous web and the second continuous web laid on each other are attached together intermittently in the carrying direction, the first edges extending in the carrying direction and being to be leg holes of each of the individual worn articles;
   a step of smoothing out, in the width direction, creases on at least one of the first continuous web and the second continuous web after the first attachment step; and
   a second attachment step, in which the first continuous web and the second continuous web are attached together at least at portions of second edges opposite to the first edges, with the creases being smoothed out.

2. The method for manufacturing a worn article according to claim 1, wherein in the folding step, each of the absorbent bodies is folded in two so that the first edges are in a predetermined positional relationship with each other.

3. The method for manufacturing a worn article according to claim 1, wherein in the second attachment step, the first continuous web and the second continuous web are attached together across an extent from the first edges to the second edges.

4. The method for manufacturing a worn article according to claim 1, further comprising a holding step of suppressing or preventing a movement, in the width direction, of the portions of the first edges, which have been attached together in the first attachment step.

5. The method for manufacturing a worn article according to claim 1, further comprising, after the step of folding in two and before the first attachment step,
   a step of previously smoothing out creases on the one of the first continuous web and the second continuous web in the width direction, intended for portions of the one of the first continuous web and the second continuous web that are to be attached together in the first attachment step.

6. A device for manufacturing individual worn articles from a continuous laminate, the continuous laminate including a first continuous web to be one torso portion of each of the worn articles, a second continuous web to be another torso portion of each of the worn articles, and a plurality of absorbent bodies provided so as to bridge in a width direction between the first continuous web and the second continuous web, the device comprising:
- a carrying device for carrying the continuous laminate in a first carrying direction extending along a direction in which the first continuous web and the second continuous web are continuous;
- a folding device for folding, in two, the continuous laminate at each of the absorbent bodies so that the first continuous web and the second continuous web are laid on each other;
- a first attachment device, by which portions of respective first edges of the first continuous web and the second continuous web laid on each other are attached together intermittently in the first carrying direction, the first edges extending in the first carrying direction and being to be leg holes of the worn article;
- at least one inclined roller, placed on an inclined axis that is inclined with respect to a primary axis direction perpendicular to the first carrying direction, for smoothing out creases on at least one of the first continuous web and the second continuous web in the width direction; and
- a second attachment device, by which the first continuous web and the second continuous web are attached together at least at portions of second edges opposite to the first edges, with the creases being smoothed out.

7. The manufacturing device according to claim 6, wherein:
- the at least one inclined roller is placed so as to be in contact with one of the second edges of the one of the first continuous web and the second continuous web; and
- a second carrying direction of the inclined roller extends toward another one of the second edges of another one of the first continuous web and the second continuous web while extending downstream in the first carrying direction.

8. The manufacturing device according to claim 7, further comprising a roller to be in contact with the other one of the first continuous web and the second continuous web so as to provide a same distance increase to a carrying path of the other one of the first continuous web and the second continuous web as an increase to a carrying distance of the one of the first continuous web and the second continuous web, which is incurred by being carried in contact with the inclined roller.

9. The manufacturing device according to claim 6, further comprising a holding device for suppressing or preventing a movement, in the width direction, of the portions of the first edges, which have been attached together by the first attachment device.

10. The manufacturing device according to claim 6, further comprising a crease smoothing-out device for straightening, in the width direction, creases on the portions of the first edges that are to be attached together by the first attachment device.

* * * * *